(12) United States Patent
Murray et al.

(10) Patent No.: US 6,537,271 B1
(45) Date of Patent: Mar. 25, 2003

(54) BALLOON CRYOGENIC CATHETER

(75) Inventors: David R. Murray, Castle Rock, CO (US); Hong Li, San Diego, CA (US)

(73) Assignee: CryoGen, Inc., San Diego, CA (US)

( * ) Notice: Subject to any disclaimer, the term of this patent is extended or adjusted under 35 U.S.C. 154(b) by 0 days.

(21) Appl. No.: 09/611,240

(22) Filed: Jul. 6, 2000

(51) Int. Cl.[7] .............................................. A61B 18/18
(52) U.S. Cl. .......................................... 606/21; 606/23
(58) Field of Search ........................ 606/20–27; 128/898

(56) References Cited

U.S. PATENT DOCUMENTS

| | | | |
|---|---|---|---|
| 3,125,096 A | | 3/1964 | Antiles et al. |
| 4,190,033 A | | 2/1980 | Foti |
| 5,190,540 A | | 3/1993 | Lee |
| 5,281,215 A | * | 1/1994 | Milder .......................... 606/20 |
| 5,486,208 A | | 1/1996 | Ginsburg |
| 5,624,392 A | | 4/1997 | Saab |
| 5,868,735 A | * | 2/1999 | Lafontaine .................... 606/21 |
| 5,971,979 A | * | 10/1999 | Joye et al. .................... 128/898 |
| 6,126,684 A | * | 10/2000 | Gobin et al. ................. 604/113 |
| 6,270,493 B1 | * | 8/2001 | Lalonde et al. ................ 606/23 |
| 6,283,959 B1 | * | 9/2001 | Lalonde et al. ................ 606/21 |

* cited by examiner

Primary Examiner—Roy D. Gibson
(74) Attorney, Agent, or Firm—Gerald W. Spinks

(57) ABSTRACT

A method and apparatus for inflating a balloon at a distal portion of an elongated delivery catheter to contact surrounding biological tissue, and expanding a refrigerant adjacent the balloon to cool the biological tissue to render it non-viable. The inflation of the balloon can be accomplished with the expanded refrigerant or with a separate pressurized fluid. The balloon can act as a heat transfer element, or there can be a separate heat transfer element on the catheter adjacent the balloon. The apparatus can be used to perform a dilation procedure, such as angioplasty, in conjunction with cooling of the surrounding tissue.

19 Claims, 2 Drawing Sheets

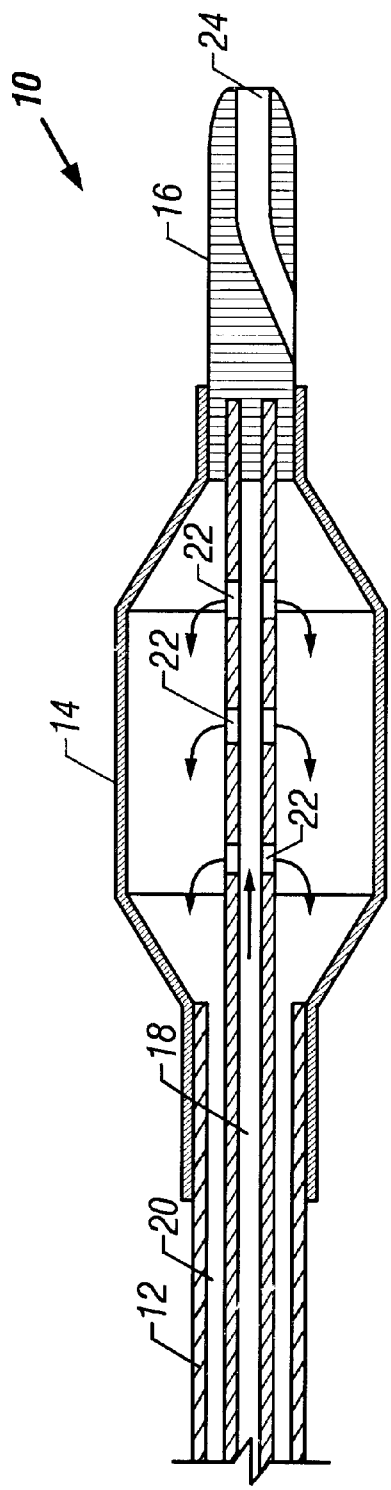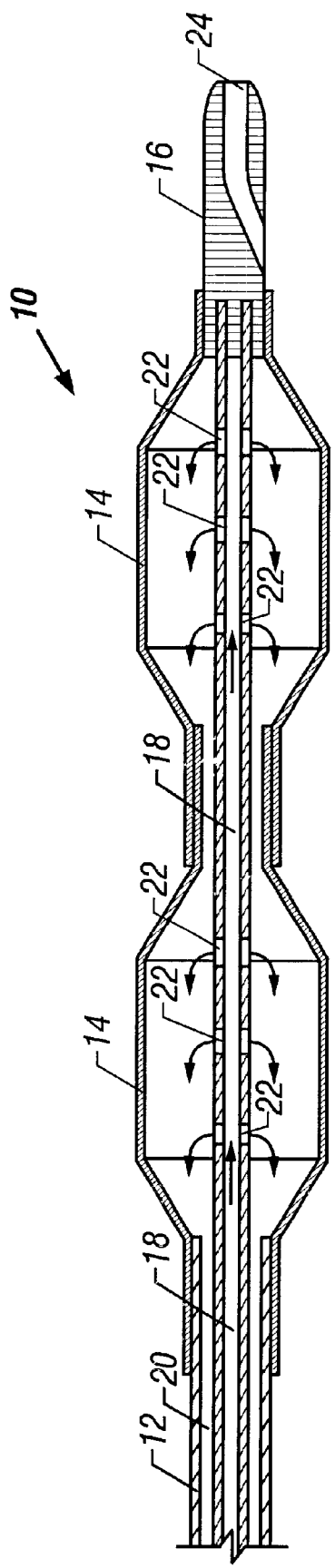

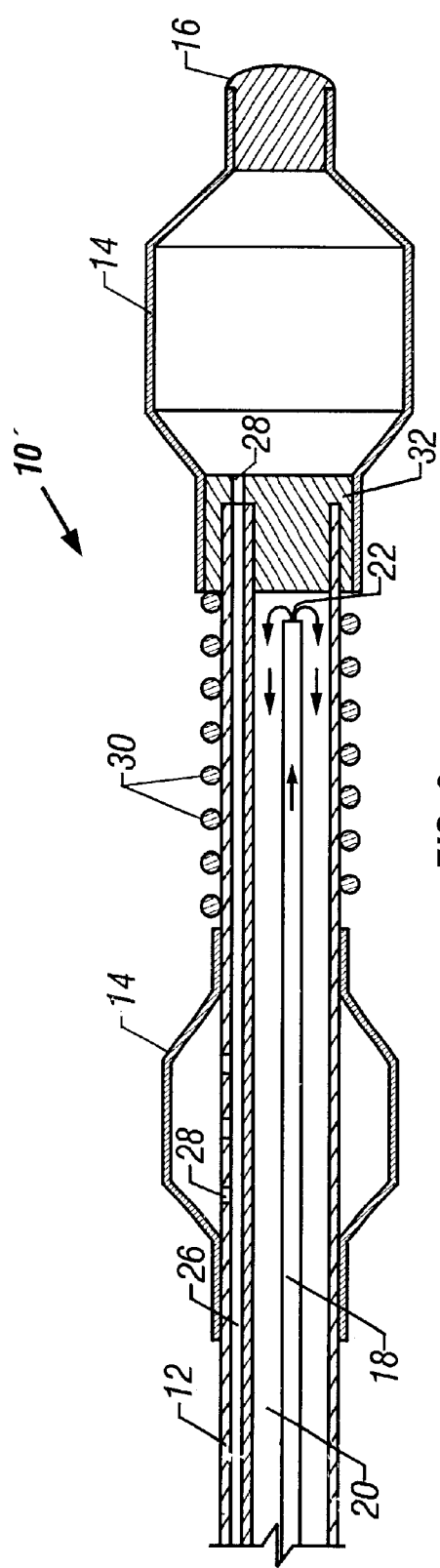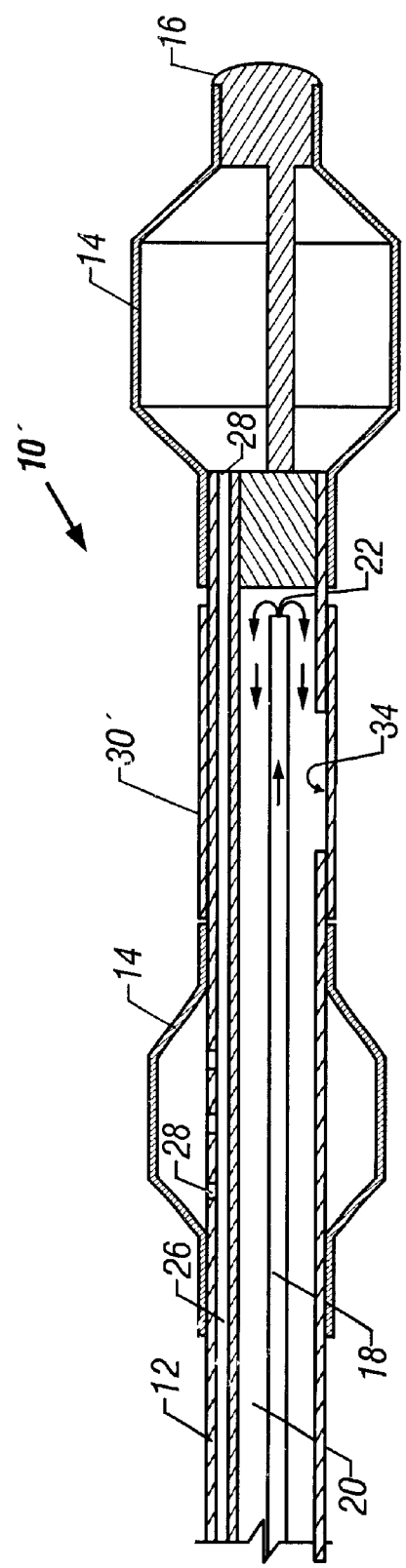

BALLOON CRYOGENIC CATHETER

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention is in the field of equipment and procedures used to apply cooling to living tissue for the purpose of causing, at a minimum, retardation of the proliferation and healing of the tissue. In certain cases, it will be desirable to freeze the tissue so as to render it non-viable.

2. Background Information

In several systems of the body of a patient, it can be desirable to apply extreme cooling to the living tissues, thereby retarding proliferation and healing of the tissues, or rendering the tissues non-viable. The non-viable tissue may then slough off for eventual removal or disintegration, or the tissue may remain in place. Some systems in which this process may be performed are the cardiovascular system and the female reproductive system. In applying this extreme cooling, it is known to introduce a refrigerant through a flexible transvascular catheter, or through a rigid probe. In known systems, the cooling is then applied to the target tissue with a heat transfer element formed as a part of the catheter or probe.

In known systems, the heat transfer element is generally limited to applying the cooling at a relatively small location, since the heat transfer element must be small enough to permit its easy introduction into the treatment area. This means that it may be necessary to apply cooling for a relatively long period of time, in order to freeze surrounding fluid in the system, such as blood in an artery or vein, before the cooling power is applied to the actual target tissue. Alternatively, it may be necessary to shift the heat transfer element to several locations, with repetitive cooling steps, in order to cover the entire target area. It would be helpful, then, to have an apparatus and procedure which will place a heat transfer element which is large enough to contact all the target tissue directly, at one time, thereby allowing the freezing of all the target tissue in one step.

Also in known systems, the application of cooling power to the target tissue may be reduced by the flow of warm fluid past the target area, such as blood flowing past an area of target tissue in an artery or vein. It would be helpful, then, to have an apparatus and procedure which will block the flow of any surrounding fluid, to accelerate the freezing process in the target tissue.

One procedure which could benefit from the freezing of tissue is the practice of angioplasty, in which a balloon is inflated to open up a region of stenosis in an artery supplying blood to the heart. It is commonly known that, after the performance of the angioplasty procedure, the area of stenosis will often experience restenosis. It would be helpful, then, to have an apparatus and procedure to freeze the arterial wall tissue in the area of the stenosis, thereby rendering it non-viable, to prevent restenosis.

BRIEF SUMMARY OF THE INVENTION

By way of example, the subject invention provides an apparatus and a method for inserting a balloon catheter into a selected location in a vascular system of a patient. When the balloon is positioned in the selected location, the balloon is inflated to contact the walls of the vascular system, such as the walls of a blood vessel. This inflation may, for example, be achieved by expanding a compressed refrigerant into the balloon, or it may be achieved by introducing a separate pressurized fluid through the catheter into the balloon. The expanded refrigerant cools either the balloon or a separate heat transfer element, to freeze the surrounding tissue. Where used, the separate heat transfer element can be a metallic coil wound around the catheter next to the balloon, or a metallic cylinder on the outside surface of the catheter next to the balloon. If the inflated balloon is used as the heat transfer device, the cooling is applied directly to the walls of the vascular system. If a separate heat transfer element is used, freezing of surrounding fluid in the vascular system, such as blood, may be necessary, forming an ice ball which will ultimately freeze the walls of the vascular system. The apparatus and method of the invention may be used, for example, to open restricted areas of a blood vessel.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIG. 1 is a longitudinal section view of a first embodiment of the apparatus according to the present invention;

FIG. 2 is a longitudinal section view of an embodiment similar to FIG. 1, with two inflatable balloons;

FIG. 3 is a longitudinal section view of a second embodiment of the apparatus according to the present invention, with a metallic coil heat transfer element; and FIG. 4 is a longitudinal section view of an embodiment similar to FIG. 3, with a metallic cylinder heat transfer element rather than a metallic coil.

DETAILED DESCRIPTION OF THE INVENTION

As shown in FIG. 1, a first embodiment of the apparatus 10 of the present invention includes a delivery element 12, an inflatable balloon 14, a refrigerant supply lumen 18, a refrigerant return lumen 20, and one or more expansion elements 22, shown as orifices in the supply lumen 18. The delivery element 12 can be an elongated flexible catheter or an elongated rigid probe. The delivery element 12 is shown as a multi-lumen element with coaxial conduits, but it also could be a bundle of separate conduits, or a bundle of separate conduits attached to a guiding element. The balloon 14 is attached adjacent to the distal end 16 of the delivery element 12. The distal end 16 of the delivery element 12 can be a formable tip or a remote manipulator, to aid in guiding the delivery element 12 through the system of a patient. Where the delivery element 12 is a flexible catheter, the distal end 16 of the delivery element 12 can be provided with a guidewire channel 24, facilitating the insertion of the catheter through the vascular system of a patient. The distal portion of the delivery element 12 and the balloon 14 can also be provided with instrumentation, such as a thermocouple.

The apparatus 10 may include a plurality of balloons 14, as shown in FIG. 2, with, for example, refrigerant being expanded into the interior of each balloon.

The delivery element 12, with the balloon 14 in a collapsed state, is passed into a selected system of a patient, such as a vascular system. This process can be aided by the use of a remote manipulator tip or formable tip on the distal end 16 of the delivery element 12. When the distal end 16 of the delivery element 12 has been placed at a selected location in the system of a patient, next to targeted biological tissues, a source of compressed refrigerant, such as a compressor or pressure bottle (not shown), can be used to flow compressed refrigerant through the supply lumen 18 of the delivery element 12. The compressed refrigerant undergoes expansion through one or more expansion elements, such as the orifices 22, near the distal end 16 of the delivery element 12, thereby lowering the temperature of the refrigerant to a desired, lower, temperature, which is sufficiently cold to freeze the target tissues. The expanded refrigerant passes into the interior of the balloon 14, thereby expanding the balloon 14.

When expanded, the balloon 14 may contact the targeted tissues, such as the walls of a blood vessel. This reduces or blocks the flow of any fluid in the vascular system, such as blood flow, and it achieves an intimate contact with the walls of the system of the patient. The expanded refrigerant cools the walls of the balloon 14, which in turn cools the targeted tissues, preferably to a temperature sufficient to retard proliferation and/or healing of the tissue or render the tissue non-viable, for example, to a temperature below their freezing point. Expanded refrigerant escapes from the balloon through the return lumen 20, to return to the inlet of the refrigerant source. Circulation of the refrigerant is continued, to maintain the temperature of the balloon 14 at the desired temperature to insure freezing of the targeted tissue.

As an alternative, a separate source (not shown) of pressurized inflation fluid can first be used to inflate the balloon 14 through the supply lumen 18 or the return lumen 20, followed by introduction of the refrigerant as described above, to achieve the freezing temperature.

FIG. 3 shows a second embodiment of the apparatus 10' of the present invention, which includes a delivery element 12, two inflatable balloons 14, a refrigerant supply lumen 18, a refrigerant return lumen 20, and an expansion element 22, shown as an orifice or the open end of a capillary tube containing the supply lumen 18. A single inflatable balloon 14 can also be used. In this embodiment, the delivery element 12 also includes an inflation lumen 26 connected to an inflation fluid source (not shown). The inflation lumen 26 has one or more inflation ports 28 exposed to the interiors of the balloons 14.

The delivery element 12 can be an elongated flexible catheter or an elongated rigid probe. The delivery element 12 is shown as a multi-lumen element, but it also could be a bundle of separate conduits, or a bundle of separate conduits attached to a guiding element. The balloons 14 are attached adjacent to the distal end 16 of the delivery element 12. The distal end 16 of the delivery element 12 can be a formable tip or a remote manipulator, and it can be provided with a guidewire channel, as discussed above. The distal portion 16 of the delivery element 12 and the balloons 14 can also be provided with instrumentation, such as a thermocouple.

Also provided in this embodiment is a separate heat transfer element 30, which can be a metallic coil formed around the delivery element 12 between the balloons 14. Rather than being within the balloons 14, as above, the expansion element 22 in this embodiment may be within the heat transfer element 30 on the delivery element 12. In this embodiment, a plug 32, made of a conductive material such as metal, is provided on the delivery element 12 where it will be exposed to the expanded refrigerant issuing from the expansion element 22. This cools the plug 32, which in turn cools the metallic coil 30, by contact therewith.

Alternatively, the heat transfer element can be a metallic tube 30' surounding the delivery element 12 between the balloons 14, as shown in FIG. 4. One or more openings 34 are provided in the delivery element 12, to expose the metallic tube 30' to the expanded refrigerant issuing from the expansion element 22. This cools the metallic tube 30'.

The delivery element 12, with the balloons 14 in a collapsed state, is passed into a selected system of a patient, such as a vascular system. This process can be aided by the use of a remote manipulator tip or formable tip on the distal end 16 of the delivery element 12, as discussed above relative to the first embodiment. When the distal end 16 of the delivery element 12 has been placed at a selected location in the system of a patient, next to targeted biological tissues, inflation fluid is introduced throught the inflation lumen 26 to inflate the balloons 14 against the walls of the surrounding organ or vessel. This reduces or blocks the flow of any fluid in a vascular system, such as blood flow.

A source of compressed refrigerant, such as a compressor or pressure bottle (not shown), can be used to flow compressed refrigerant through the supply lumen 18 of the delivery element 12. The compressed refrigerant undergoes expansion through the orifice 22, near the distal end 16 of the delivery element 12, thereby lowering the temperature of the refrigerant to a desired, lower, temperature, which is sufficiently cold to freeze the target tissues. The expanded refrigerant passes through the expansion element 22, thereby cooling the heat transfer element 30, 30' which in turn cools the fluid in the surrounding vascular system, forming an ice ball. The ice ball in turn cools the targeted tissues below their freezing point. Formation of the ice ball is facilitated by blockage of the flow of the surrounding fluid by the balloons 14. Expanded refrigerant returns through the return lumen 20, to the inlet of the refrigerant source. Circulation of the refrigerant is continued, to maintain the temperature of the heat transfer element 30, 30' at the desired temperature to insure freezing of the targeted tissue.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for cooling biological tissue in a patient, comprising:

a source of compressed refrigerant, said source having an inlet and an outlet;

an elongated delivery element;

an inflatable balloon affixed to a distal portion of said delivery element;

a supply conduit on said delivery element, said supply conduit connecting said outlet of said refrigerant source to said distal portion of said delivery element;

an expansion element connected to a distal portion of said supply conduit for expanding compressed refrigerant; and a return conduit on said delivery element, said return conduit connected to return expanded refrigerant from an outlet of said expansion element to said inlet of said refrigerant source;

wherein said delivery element comprises a rigid probe.

2. An apparatus for cooling biological tissue in a patient, comprising:
- a source of compressed refrigerant, said source having an inlet and an outlet;
- an elongated delivery element;
- an inflatable balloon affixed to a distal portion of said delivery element;
- a supply conduit on said delivery element, said supply conduit connecting said outlet of said refrigerant source to said distal portion of said delivery element;
- an expansion element connected to a distal portion of said supply conduit for expanding compressed refrigerant;
- a return conduit on said delivery element, said return conduit connected to return expanded refrigerant from an outlet of said expansion element to said inlet of said refrigerant source;
- a source of pressurized fluid;
- an inflation conduit on said delivery element, said inflation conduit connecting said pressurized fluid source to the interior of said balloon; and
- a heat transfer element mounted on said distal portion of said delivery element;
- wherein said expansion element is positioned to expand refrigerant adjacent to said heat transfer element, thereby applying cooling to surrounding tissue via said heat transfer element; and
- wherein said return conduit is connected to return expanded refrigerant from the interior of said heat transfer element to said inlet of said refrigerant source.

3. An apparatus as recited in claim 2, further comprising a second inflatable balloon affixed to said distal portion of said delivery element, said second balloon being connected to said inflation conduit, and said heat transfer element being positioned between said two balloons.

4. An apparatus as recited in claim 2, wherein said heat transfer element comprises a metallic coil wound around said delivery element.

5. An apparatus as recited in claim 2, wherein said heat transfer element comprises a metallic cylinder mounted on said delivery element.

6. An apparatus for cooling biological tissue in a patient, comprising:
- a source of compressed refrigerant, said source having an inlet and an outlet;
- a source of pressurized fluid;
- an elongated flexible catheter;
- at least one inflatable balloon affixed to a distal portion of said catheter;
- an inflation lumen in said catheter, said inflation lumen connecting said pressurized fluid source to the interior of said at least one balloon;
- a heat transfer element mounted on said distal portion of said catheter adjacent said at least one balloon;
- a supply lumen within said catheter, said supply lumen connected to conduct compressed refrigerant from said outlet of said refrigerant source to said distal portion of said catheter;
- an expansion element connected to said supply lumen, said expansion element being positioned to expand compressed refrigerant adjacent to said heat transfer element, thereby applying cooling to surrounding tissue via said heat transfer element; and
- a return lumen within said catheter, said return lumen connected to conduct expanded refrigerant from said interior of said heat transfer element to said inlet of said refrigerant source.

7. An apparatus as recited in claim 6, wherein said expansion element comprises at least one orifice in said supply lumen.

8. An apparatus as recited in claim 6, further comprising a steerable tip on said catheter.

9. An apparatus as recited in claim 6, further comprising a second inflatable balloon affixed to said distal portion of said catheter, said second balloon being connected to said inflation lumen, and said heat transfer element being positioned between said two balloons.

10. An apparatus as recited in claim 6, wherein said heat transfer element comprises a metallic coil wound around said catheter.

11. An apparatus as recited in claim 6, wherein said heat transfer element comprises a metallic cylinder mounted on said catheter.

12. A method for cooling biological tissue in a patient, said method comprising:
- providing an elongated delivery element with an inflatable balloon affixed to a distal portion thereof;
- inserting said delivery element and said balloon into a target location within said patient;
- flowing compressed refrigerant through said delivery element;
- inflating said balloon to contact selected biological tissues; and
- expanding said refrigerant adjacent said distal portion of said delivery element to cool selected biological tissues;
- wherein:
  - said inflation of said balloon comprises conducting a pressurized fluid through an inflation lumen of said delivery element into the interior of said balloon; and
  - said expansion of said refrigerant cools a heat transfer element on said delivery element adjacent said balloon to cool selected biological tissues.

13. A method of opening a restricted area of a blood vessel, comprising
- providing an elongated catheter with an inflatable balloon affixed to a distal portion thereof;
- inserting said catheter and said balloon into a target location within said blood vessel;
- inflating said balloon to dilate said blood vessel;
- flowing compressed refrigerant through said catheter;
- expanding said refrigerant adjacent said distal portion of said catheter to cool said dilated portion of said blood vessel;
- wherein:
  - said inflation of said balloon comprises conducting a pressurized fluid through an inflation lumen of said catheter into the interior of said balloon; and
  - said expansion of said refrigerant cools a heat transfer element on said catheter adjacent said balloon to cool said dilated portion of said blood vessel.

14. A method for opening a restricted area of a blood vessel, comprising:
- providing an elongated catheter with an inflatable balloon affixed to a distal portion thereof;
- inserting said catheter and said balloon into a target location within said blood vessel;

inflating said balloon to dilate said blood vessel;

flowing compressed refrigerant through said catheter;

expanding said refrigerant adjacent said distal portion of said catheter to cool said dilated portion of said blood vessel;

wherein:

said inflation of said balloon comprises conducting a pressurized fluid through an inflation lumen of said catheter into the interior of said balloon; and said expanded refrigerant is conducted into the interior of said inflated balloon, to cool the surface of said balloon to cool said dilated portion of said blood vessel.

15. A method for rendering non-viable selected biological tissue in a patient, said method comprising:

inserting an elongated delivery element having an inflatable balloon into the patient;

inflating said balloon adjacent to the selected biological tissue; and rendering non-viable said selected biological tissues by cooling at least a portion of said elongated delivery element;

wherein:

said elongated delivery element has a metallic coil; and said cooling is applied to said metallic coil.

16. A method for rendering non-viable selected biological tissue in a patient, said method comprising:

inserting an elongated delivery element having an inflatable balloon into the patient;

inflating said balloon adjacent to the selected biological tissue; and rendering non-viable said selected biological tissues by cooling at least a portion of said elongated delivery element;

wherein:

said elongated delivery element has a metallic tube; and said cooling is applied to said metallic tube.

17. A method for rendering non-viable selected biological tissue in a patient, said method comprising:

inserting an elongated delivery element having an inflatable balloon into the patient;

inflating said balloon adjacent to the selected biological tissue; and rendering non-viable said selected biological tissues by cooling at least a portion of said elongated delivery element;

wherein said inserting comprises inserting an elongated delivery element having a pluralty of inflatable balloons into the patient.

18. A method for opening a restricted area of a blood vessel, comprising:

inserting an elongated delivery element having an inflatable balloon into a blood vessel of a patient;

inflating said balloon to dilate said blood vessel; and rendering non-viable selected tissues of said blood vessel by cooling at least a portion of said elongated delivery element;

wherein:

said elongated delivery element has a metallic coil; and said cooling is applied to said metallic coil.

19. A method for opening a restricted area of a blood vessel, comprising:

inserting an elongated delivery element having an inflatable balloon into a blood vessel of a patient;

inflating said balloon to dilate said blood vessel; and rendering non-viable selected tissues of said blood vessel by cooling at least a portion of said elongated delivery element;

wherein:

said elongated delivery element has a metallic tube; and said cooling is applied to said metallic tube.

\* \* \* \* \*